United States Patent
Pruitt et al.

(10) Patent No.: US 10,472,604 B2
(45) Date of Patent: Nov. 12, 2019

(54) FEED MATERIAL FOR BIOMASS GENERATOR

(71) Applicant: NCH Corporation, Irving, TX (US)

(72) Inventors: Judith G. Pruitt, Mesquite, TX (US); Robert Clarence Pearce, III, Irving, TX (US); John Ray Roheim, Flower Mound, TX (US)

(73) Assignee: NCH Corporation, Irving, TX (US)

( * ) Notice: Subject to any disclaimer, the term of this patent is extended or adjusted under 35 U.S.C. 154(b) by 231 days.

(21) Appl. No.: 15/363,628

(22) Filed: Nov. 29, 2016

(65) Prior Publication Data

US 2017/0073632 A1 Mar. 16, 2017

Related U.S. Application Data

(60) Continuation of application No. 14/262,377, filed on Apr. 25, 2014, now Pat. No. 9,540,608, which is a division of application No. 11/550,185, filed on Oct. 17, 2006, now abandoned.

(60) Provisional application No. 60/796,487, filed on May 1, 2006.

(51) Int. Cl.
| | |
|---|---|
| *C12N 1/20* | (2006.01) |
| *C02F 3/34* | (2006.01) |
| *C22B 1/24* | (2006.01) |
| *C22B 3/18* | (2006.01) |

(52) U.S. Cl.
CPC ............... *C12N 1/20* (2013.01); *C02F 3/341* (2013.01); *C02F 3/348* (2013.01); *C22B 1/24* (2013.01); *C22B 3/18* (2013.01); *Y02P 10/234* (2015.11)

(58) Field of Classification Search
None
See application file for complete search history.

(56) References Cited

U.S. PATENT DOCUMENTS

| | | |
|---|---|---|
| 3,242,055 A | 3/1966 | De Lucia |
| 3,728,445 A | 4/1973 | Bardani |
| 4,810,385 A | 3/1989 | Hater et al. |
| 5,275,943 A | 1/1994 | DiTuro |
| 5,283,059 A * | 2/1994 | Suzuki ............ C12N 1/04 424/93.46 |
| 5,401,501 A | 3/1995 | Pratt |
| 5,426,024 A | 6/1995 | Flores-Cotera et al. |
| 5,447,866 A | 9/1995 | Runyon |
| 5,516,687 A * | 5/1996 | Perez ............ C02F 3/343 210/532.2 |
| 5,716,630 A | 2/1998 | Lin et al. |
| 5,770,079 A | 6/1998 | Haase |
| 5,911,877 A | 6/1999 | Perez et al. |
| 5,998,184 A | 12/1999 | Shi |
| 6,190,591 B1 | 2/2001 | van Lengerich |
| 6,254,886 B1 * | 7/2001 | Fusca ............ A23L 29/065 424/464 |
| 6,280,719 B1 | 8/2001 | Suh |
| 6,325,934 B1 * | 12/2001 | Tobey, Jr. ............ C02F 3/34 210/606 |
| 6,335,191 B1 | 1/2002 | Kiplinger et al. |
| 6,544,552 B2 | 4/2003 | Sparks et al. |
| 6,562,585 B1 | 5/2003 | Hiatt |
| 6,620,611 B2 * | 9/2003 | Hince ............ B09C 1/002 210/600 |
| 6,723,526 B1 | 4/2004 | Hernandez et al. |
| 6,733,781 B2 | 5/2004 | Abu-Izza et al. |
| 7,029,699 B2 | 4/2006 | Robinson et al. |
| 7,037,708 B1 | 5/2006 | Runge et al. |
| 2004/0208981 A1 | 10/2004 | Wong |
| 2005/0032032 A1 | 2/2005 | Pearce, III et al. |

OTHER PUBLICATIONS

Xu et al., Production of alkali-tolerant cellulase-free xylanase by *Pseudomonas* sp. WLUN024 with wheat bran as the main substrate, published 2005 in the World Journal of Microbiology and Biotechnology, vol. 21, pp. 575-581.

* cited by examiner

*Primary Examiner* — Vera Afremova
(74) *Attorney, Agent, or Firm* — Ross Barnes LLP; Robin L. Barnes

(57) ABSTRACT

The present invention is a bacteria and nutrient delivery composition containing bran. The subject composition is preferably made in the form of a tablet that is structurally stable without being excessively hard. The tablets preferably have a configuration that reduces the likelihood of premature shearing in tableting presses or jamming in feeder devices for biomass generators. Methods of manufacturing the bacterial delivery composition in a structurally stable form that maintains bacterial viability are also provided.

26 Claims, 1 Drawing Sheet

FEED MATERIAL FOR BIOMASS GENERATOR

CROSS-REFERENCE TO RELATED APPLICATIONS

This application is a continuation of U.S. application Ser. No. 14/262,377 filed on Apr. 25, 2014, which is a divisional of U.S. application Ser. No. 11/550,185, filed Oct. 17, 2006, which claims the benefit of U.S. Provisional Patent Application No. 60/796,487 filed May 1, 2006.

BACKGROUND OF THE INVENTION

The present invention relates generally to tableted blends of bran and at least one waste-decomposing microorganism for use as a starter material for biomass generators.

Bacteria decompose organic materials in the environment in a natural process that typically degrades organic material into carbon dioxide and water. Under normal conditions, competition for resources, limited supplies of nutrients, and natural enemies can combine to inhibit rapid bacterial growth that in turn limits organic material decomposition. Bacteria proliferate rapidly when selected strains of bacteria are isolated and provided a growth-promoting food source. These larger bacterial populations decompose waste material more quickly and effectively and can be used in a wide variety of applications, such as, for example, in septic tanks, grease traps, drains, RV holding tanks, cesspools, lagoons, ponds, outdoor toilets, portable toilets and the like, which tend to collect waste present in various forms such as proteins, carbohydrates (such as cellulose), and lipids such as fats and oils.

Most conventional bacteria or biomass growth or generation devices, such as those disclosed in, for example, U.S. Pat. No. 6,335,191 and other patents citing or cited iCn it, use a starter material comprising at least one selected beneficial bacterial strain and enough of a suitable bacteria food source to grow the bacteria from a starter population to a utility population that is large enough to sustain growth and promote a desired end use application when discharged from this device into a waste material or other media containing another viable food source. Conventional, commercially available sources of starter bacteria occur in liquid, powder or other solid form. Some starter bacteria are already combined with a starter nutrient and others require mixture with a separate starter nutrient, most often in an aqueous suspension.

Solid nutrient forms are preferred because they provide a bacteria starter population in a form that provides stable storage, easier handling, and low overall cost. However, solid nutrients may be friable, depending upon their components, and too readily disintegrate into powders that are easily inhaled, jam machine parts, or are messy to apply to septic systems, etc. Solid forms that are not friable when initially produced may subsequently become friable and deteriorate rapidly in humid environments. This is particularly the case with conventional solid nutrients incorporating bran, a desirable feed material. Other pelletized solid forms are too hard, which can adversely affect solubility or damage automated feeders or stirring devices.

Many methods of manufacturing and packaging bacteria are also difficult to use or compromise bacterial viability. For example, continuous milling or direct extrusion methods can involve temperatures that kill bacteria or compromise their viability, however, temperature-neutral methods can also kill or compromise bacteria where tablets are manufactured under pressures greater than bacteria can withstand. On the other hand, if pressures are too low, tablets will lack structural integrity.

Accordingly, a pelletized feed material is needed that does not require temperatures and pressures that adversely affect waste-decomposing bacterial viability and that provides a structurally stable and readily usable solid tablet form containing bran.

SUMMARY OF THE INVENTION

The present invention is a bacteria and nutrient delivery composition containing bran that is preferably made in the form of a tablet that is structurally stable without compromising bacterial viability. The tablets preferably have a configuration that reduces the likelihood of premature shearing in tableting presses or jamming in feeder devices for biomass generators. A method of manufacturing the bacterial delivery composition in a structurally stable form that maintains bacterial viability is also disclosed.

According to one preferred embodiment of the invention, a tablet is disclosed that comprises bran and at least one waste-decomposing microorganism and minimal growth-promoting nutrients in relative proportions in a tablet having preferred compression ranges.

According to another embodiment of this invention, a method of manufacturing a bran and microorganism waste-decomposing tablet is disclosed that comprises preferred steps that provides for a composition well-suited for formation as a durable tablet form.

According to another embodiment of this invention, a method of manufacturing a bran and microorganism waste-decomposing tablet that is made within defined compression ranges that provides for a tablet that is non-friable yet not excessively hard that will not dissolve in its targeted environment nor will kill or compromise the bacteria.

BRIEF DESCRIPTION OF THE DRAWINGS

A preferred embodiment of the invention is further described and explained in relation to the following drawings wherein.

DETAILED DESCRIPTION OF THE INVENTION

The present invention is a bacterial and nutrient delivery composition containing bran made in the form of a tablet that is structurally stable but readily dissolvable and manufactured in a form that makes the tablet more easily removable from its press.

The tablet has a configuration that reduces the likelihood of premature shearing in tableting presses, and jamming in feeder devices for biomass generators. A problem tablet manufacturers face is the removal of a tablet after it is pressed in a manner that does not chip the tablet or damage the equipment. The typical tablet press has an arm that pushes the tablet out of the press. During removal of the tablet, however, and depending upon the tablet's shape, the arm may chip the tablet or glance it leaving it within the press and possibly damaging the arm. In further efforts to develop a more structurally stable bran and bacterial waste-decomposing tablet, a tablet has been designed that is preferred for tablet press removal.

Figure 1:
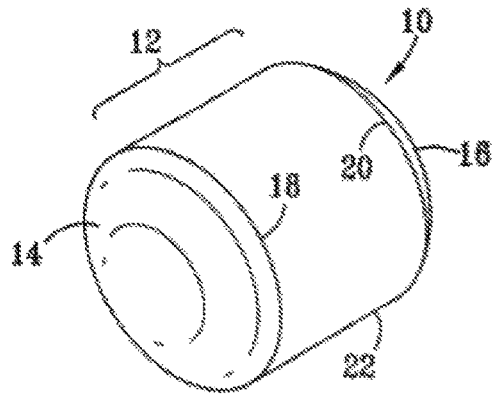
FIG. 1 is a perspective view of a preferred embodiment of the pellet-shaped tablet.

Such a tablet is exemplified in FIGS. 1-5. FIG. 1 shows tablet 10 having a cylindrical portion 12 and ends 14 and 16, better shown in FIG. 2. Ends 14 and 16 are preferably curved outwardly (convex) from the cylindrical portion to prevent tablets from stacking upon each other, particularly if used in a feeding bin, such as a semi-automated feeding system used to breakdown fats and organic matter in grease traps, where the tablets could jam or force packing. It is also preferable that the tablet has defined edges 18 and 20 separating the ends, but more importantly, that the outer circumference 22 comprises at least some portion that is perpendicular to the radius of cylindrical portion 12. This permits the tablet press arm described above to sufficiently contact the tablet to displace it from the press.

Figure 2:
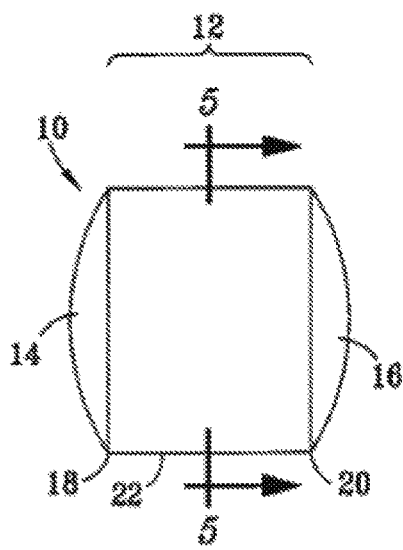
FIG. 2 is a side elevation view of the pellet-shaped tablet of FIG. 1.
Figure 3:
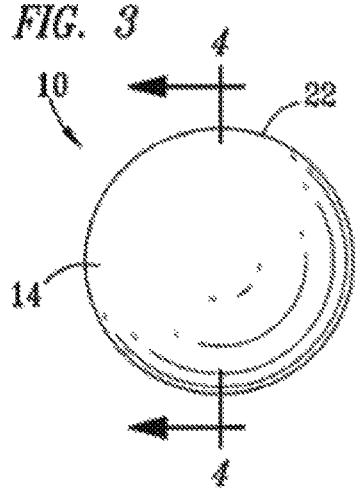
FIG. 3 is a front elevation view of the pellet-shaped tablet of FIG. 1.
Figure 4:
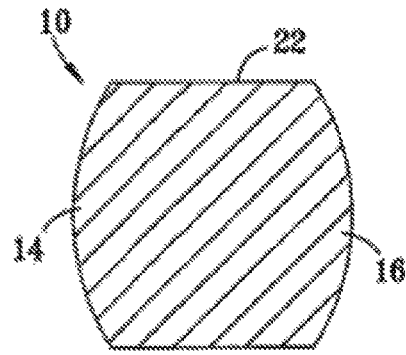
FIG. 4 is a cross-sectional view taken along line 4-4 of FIG. 3.
Figure 5:
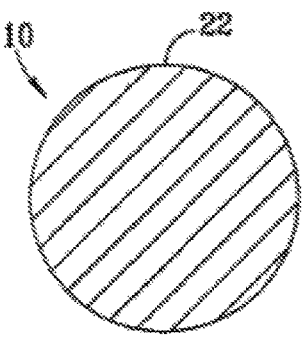
FIG. 5 is a cross-sectional taken along line 5-5 of FIG. 2.

A preferred embodiment of the overall dimensions of tablet 10 is shown in Table 1. While Table 1 provides specific dimensions, various sizes are contemplated and it is the overall proportion that is particularly advantageous. The shape of tablet 10 can be expressed as a ratio of the length of the tablet along its longitudinal axis, defined as the distance between end 14 and end 16 (and including the length of cylindrical portion 12), to the diameter across the cylindrical portion 12 (FIGS. 2 and 4). The preferred range for the length to width (diameter) ratio of the tablet is between 0.9 and 1.2, and the preferred length of the longitudinal axis is between about 0.25 inches and 0.68 inches, and is about 0.266 inches in the preferred embodiment. If ends 14 and 16 are curved, the curvature is preferably slight so that the combined distance between the outermost point of each end and the nearest point of cylindrical portion 12 along its longitudinal axis is termed the "cup depth". In the preferred embodiment, the cup depth is between about 0.018 inches and 0.048 inches and preferably about 0.033 inches, and in relation to the tablet, it is preferably about four times or less than the total length of tablet 10. A preferred range for a radius of curvature of each end 14 or 16 is between 0.2 inches and 0.3 inches, and the preferred embodiment has a radius of curvature of about 0.25 inches.

TABLE 1

| | |
|---|---|
| Weight (grams) | 0.233 +/− 0.0125 |
| Length (inches) | 0.266 +/− 0.0118 |
| Diameter (inches) | 0.25 +/− 0.0118 |
| End to End Compression (kilopond) | 7.0 +/− 1.50 |
| Barrel Compression (kilopond) | 6.0 +/− 1.50 |
| Cup Depth (inches) | 0.033 +/− 0.015 |
| Radius of Curvature (inches) | 0.253 +/− 0.5 |

Tablet 10 preferably comprises at least one waste-decomposing microorganism and also includes bran as a bacterial growth substrate. The preferred proportion of bran in the composition is less than about 2% of the total weight percent of tablet 10 and the bacterial cultures can be any suitable amount, but is between 0.1% and 10% of the total weight of the tablet. Example 1 provides the general relative proportions and Example 2 provides a preferred embodiment of the invention's composition.

Bran is a preferred component of tablet 10. The concentrated bran component results in tablets that are structurally stable for longer periods and possess greater durability. Bran also absorbs moisture within the targeted environment and fosters the tablet's disintegration and also provides a growth substrate for the bacteria as it forms a utility population adequate to decompose waste. Wheat bran is preferred, although other water-absorbing organic matter upon which bacteria thrive is also acceptable.

Waste-decomposing microorganisms useful in tablet 10 can include either spore forming or vegetative bacteria. A plurality of various bacterial forms can also be desirable for use in the generation of a bacterial delivery package for application in various effluent streams. For instance, spore forming and vegetative bacterial forms are desirable in a single package, preferably accomplished by using spray-dried bacteria in bran culture. Spore-forming bacteria are preferable because of their natural stability and their small, consistent particle size is also consistent with the micronized bacteria medium that permits a uniform particle distribution within the tablet and improves its structural integrity. In tableting processes, small consistent particles enhance the compression process presented below. Non-spore-forming bacteria grown on bran particles are less consistent, and are more irregular in shape, densities, sizes, and substrate characteristics, which make them less ideal in the tableting process than spore-forming bacteria.

However, waste-decomposing non-sporeforming bacteria can be grown and dried on a substrate, such as wheat bran when a dry, non-sporeforming bacterial culture is desired for a dry bacterial product. This process results in a stable, concentrated bran culture. For example, a preferred bran culture that contains *Pseudomonas* as a waste-decomposing non-sporeforming bacteria (referred to "EcoBionics Bran Culture" in-house and in Example 2) is prepared in the following manner: bran (wheat shorts) are autoclaved to kill background microorganisms, then growth medium mixed with *Pseudomonas* culture is applied to the autoclaved bran preparation. The bran-*Pseudomonas* mixture is incubated under humidity for 48 hours then dried for 72 hours to dry the mixture. The final bran culture preparation in this preferred embodiment comprises *Pseudomonas* bacteria at about $5 \times 10^9$ cfu/g, which is substantially free of other bacteria such as Salmonella, *E. coli*, and *Listeria* to provide a more structurally similar bacterial population. One of ordinary skill in the art will appreciate that other non-sporeforming bacteria may also be used.

A preferred combination of spore-forming waste-decomposing microorganisms, referred to collectively "Spore Blend" in Example 2, is about 33% AT31 *Bacillus subtilis*, about 33% AT316 *Bacillus licheniformis*, about 17.5% AT3032 *Bacillus subtilis*, and about 17.5% AT3040 *Bacillus thuringiensis*. Other suitable cultures known to one of ordinary skill in the art may also be used. The *Bacillus* strains may be spray-dried without any carrier material to achieve a dry spore powder raw material.

The composition of tablet 10 may further comprise fillers, binders, and buffers and other materials, and without limiting their function by their description, they will be referred to individually as a "base component" for ease of reference. Without limiting the invention, various examples include those derived from organic matter such as carbohydrates, proteins and lipids. Materials that can be used are well known in the art and include, for example, the following compounds and the derivatives thereof: starch, talc, microcrystalline cellulose, lactose, highly dispersed silica, polyvinylpyrrolidone, cellulose powder, mannitol, sorbitol, xylitol, glucose, sucrose, fructose, maltose, dextrose, maltodextrin, kaolin or cellulose derivatives such as methylcellulose, hydroxylpropylcellulose or hydroxypropylmethylcellulose, starch (including various forms such as pregelatinized), light anhydrous silicic acid, titanium oxide, magnesium aluminometasilicate and polyethylene glycols, as well as calcium carbonate, calcium, magnesium or glyceryl stearate. Proteins such as casein or other suitable amino acids and their peptide polymers and derivatives thereof, including various nitrogenous compounds, may also be used. Various sodium and calcium salts such as sodium chloride, sodium bicarbonate, disodium phosphate, monosodium phosphate, calcium monohydrogen phosphate, and calcium sulfate may also be used. Various oils, including hydrogenated and partially hydrogenated oils, may be used. Any suitable colorant may also be used. The tablet composition of the present invention can contain additives usually incorporated into tablet compositions in addition to the above-described ingredients so far as the effect of the present invention is not impaired.

One of ordinary skill in the art would appreciate that the proportionate compositions of the bran, at least one waste-decomposing microorganism and other components affect the overall physical properties of the tablet, such as, for example, hardness, compressibility, size, shape, etc., and that the relative compositions will be adjusted to obtain the desired physical properties, such as provided in a preferred embodiment shown in Table 1.

Example 1

| Raw Material | Weight %, Range |
| --- | --- |
| Starch | 15-30% |
| Sugar | 25-40% |
| Protein | 2-7% |
| Sodium Salt | 1-2% |
| Calcium Salt | 0.1-1% |
| Soda | 3-7% |
| Buffering agent | 2-8% |
| Phosphate salt | 0.5-2.5% |
| Nitrogen compound | 2-7% |
| Bran culture | 1-2% |
| Waste-decomposing bacteria | 0.1-10% |
| Tablet starch | 1-15% |
| Binder | 0.1-1% |

Example 2

| Raw Material | Weight % |
| --- | --- |
| Corn Starch | 24.00% |
| Dextrose | 35.30% |
| Casein | 5.00% |
| Sodium Chloride | 2.60% |
| Calcium Sulfate | 0.80% |
| Sodium Bi-carbonate | 6.40% |
| Disodium Phosphate | 6.00% |
| Monosodium Phosphate | 2.00% |
| Urea | 5.70% |
| EcoBionics Bran Culture | 1.20% |
| Spore Blend | 0.10% |
| Microcrystalline cellulose | 10.70% |
| Magnesium Stearate | 0.20% |
| TOTAL | 100.00% |

The disclosed bran and waste-decomposing bacteria composition is advantageous for use in a tablet press and as feed material for biomass generators and other applications where waste decomposition is desired. The composition is particularly desirable where a tablet that remains intact and non-friable to withstand shipping and handling and exhibits dimensions amenable for use in feed systems and its method of manufacture accomplishes these advantageous attributes of the tablet.

Methods of manufacturing the bacterial delivery composition in a structurally stable form that maintains bacterial viability are now presented. All raw materials should be stored in an environment that is no greater than about 40% humidity and where the temperature is between 45° F. and 65° F. The relatively low humidity improves the structural stability of the composition and the temperature maintains bacterial viability and promotes blending of the composition. To promote adequate blending, it is preferable that the raw materials are sized to 28-30 mesh prior to their addition. Lower mesh sizes may reduce bacterial viability and larger sizes are difficult to blend. To reduce the mesh size of bacterial cultures, a Stokes' grinder (for example, a grinder such as a bar oscillating granulator) is preferred in part because of its lesser shear and lower heat rather than other grinder types, for instance, a rotary-type grinder where the shear forces are greater. All other components, if not received at 28-30 mesh specification, may be ground with either a Fitzmill (for example, Model IR520 Chilsonator®) or Stokes Grinder or any other grinder capable of reducing the size of the constituent particles to the preferred mesh size and minimize phase separation.

The components of the preferred embodiment presented in Example 2 are blended in a preferred manner, although others may be acceptable, as follows: corn starch, dextrose, and casein are mixed in a blender for 10 minutes, followed by the addition of sodium chloride, calcium sulfate, sodium bicarbonate, disodium phosphate, monosodium phosphate, urea, microcrystalline cellulose, Spore Blend, and bran culture concentrate (pre-ground to 28-30 mesh) and mixed for about 10 minutes. Magnesium stearate is also mixed with the composition and all mixing times are approximate and may be shortened or lengthened, depending upon the materials, the relative humidity, the mesh sizes, and other factors appreciated by one of ordinary skill. The final composition is then formed using a desired tablet press adapted with dies to obtain the preferred tablet shape shown in FIGS. 1-5.

The invention claimed is:

1. A biomass generator feed material in tablet or pellet form, the feed material comprising the following ingredients:
   a dried culture of non-spore forming *Pseudomonas* on bran that is substantially free of other bacteria;
   at least one spore-forming strain of *Bacillus* without an incubation carrier;
   protein;
   sugar comprising sucrose but not dextrose;
   starch; and
   wherein the tablet or pellet comprises about 1 to 2 wt. percent bran.

2. The feed material of claim 1 wherein the ingredients are mixed throughout the tablet or pellet.

3. The feed material of claim 1 wherein the tablet or pellet is configured for use in a semi-automated feeder system without jamming by having a substantially cylindrical shape with convex ends, a length-to-diameter-ratio between about 0.9 and about 1.2, and a cup depth between about 0.018 inches and about 0.048 inches.

4. The feed material of claim 1 wherein the tablet or pellet tablet has a hardness between about 5.5 kilopond and about 8.5 kilopond.

5. The feed material of claim 1 wherein the spore-forming strain is one or more *Bacillus* species.

6. The feed material of claim 5 wherein the spore-forming strain is one or more of *Bacillis subtilis, Baccillus licheniformis, Bacillus thuringiensis, Bacillus amyloliquefaciens,* or *Bacillus simplex.*

7. The feed material of claim 1 wherein the sugar further comprises maltodextrin.

8. The feed material of claim 6 wherein the sugar further comprises maltodextrin.

9. The feed material of claim 7 wherein the tablet or pellet comprises around 2-7% protein and around 25-40% sugar by weight.

10. The feed material of claim 9 wherein the at least one spore-forming strain of waste decomposing bacteria comprises one or more species of *Bacillus* and wherein the tablet or pellet comprises around 0.1-10% of the *Pseudomonas* and *Bacillus* by combined weight.

11. The feed material of claim 1 wherein the tablet or pellet comprises around 5% protein and around 35% sugar by weight.

12. The feed material of claim 11 wherein the sugar further comprises maltodextrin.

13. The feed material of claim 1 wherein the dried bran culture preparation comprises about $5 \times 10^9$ cfu/g *Pseudomonas.*

14. The feed material of claim 9 further comprising around 0.1-11% microcrystalline cellulose by weight.

15. The feed material of claim 1 wherein the bran culture is incubated for about 48 hours.

16. The feed material of claim 15 wherein the bran culture is incubated under humidity.

17. The feed material of claim 15 wherein the bran culture is dried for about 72 hours.

18. The feed material of claim 17 wherein the dried bran culture is ground to a particle size of about 28-30 mesh.

19. The feed material of claim 1 wherein the dried bran culture is ground to a particle size of about 28-30 mesh.

20. The feed material of claim 19 wherein all other ingredients are 30 mesh or smaller.

21. The feed material of claim 1 wherein the tablet or pellet comprises around 2-7% protein, around 25-40% sugar by weight, and around 15-30% starch; and wherein the sugar further comprises maltodextrin.

22. The feed material of claim 21 further comprising around 0.1-11% microcrystalline cellulose by weight, around 0.1-1% magnesium stearate, and around 0.1-1% of the spore-forming strain of waste-decomposing bacteria comprising one or more *Bacillus* species.

23. The feed material of claim 22 wherein the ingredients are mixed throughout the tablet or pellet.

24. The feed material of claim 1 wherein the bran is autoclaved prior to culturing with the *Pseudomonas.*

25. The feed material of claim 1 wherein the dried culture comprises: autoclaved bran, non-spore forming *Pseudomonas*, and growth medium that are mixed, incubated, and dried.

26. The feed material of claim 1 wherein the tablets or pellets are non-friable and remain substantially intact through a feeder device in a biomass generator.

* * * * *